(12) United States Patent
Righettini et al.

(10) Patent No.: US 10,302,620 B2
(45) Date of Patent: May 28, 2019

(54) MEASURING DEVICE FOR MEASURING THE STICKINESS, IMPERFECTIONS AND IMPURITIES OF TEXTILE FIBERS, IN PARTICULAR COTTON FIBERS

(71) Applicant: MESDAN S.p.A., Puegnago del Garda (IT)

(72) Inventors: Antonio Righettini, Salo (IT); Giuseppe Pace, Roe Volciano (IT); Marco Musesti, Roe Volciano (IT)

(73) Assignee: MESDAN S.p.A., Puegnago del Garda (IT)

( * ) Notice: Subject to any disclaimer, the term of this patent is extended or adjusted under 35 U.S.C. 154(b) by 67 days.

(21) Appl. No.: 15/334,939

(22) Filed: Oct. 26, 2016

(65) Prior Publication Data

US 2017/0122925 A1   May 4, 2017

(30) Foreign Application Priority Data

Oct. 30, 2015 (IT) .................. 102015000067613

(51) Int. Cl.
*G01L 5/00* (2006.01)
*G01N 3/00* (2006.01)
(Continued)

(52) U.S. Cl.
CPC .......... *G01N 33/365* (2013.01); *D01G 31/003* (2013.01); *G01L 5/0085* (2013.01);
(Continued)

(58) Field of Classification Search
CPC ...... D01G 19/00–19/30; D01G 31/003; G01N 33/36–33/367; G01N 2203/0282; B65H 2701/31
(Continued)

(56) References Cited

U.S. PATENT DOCUMENTS 3,735,446 A * 5/1973 Lorenz ............... D01G 19/28
                                                    19/218
3,975,146 A * 8/1976 Saupe ................ G03G 15/2014
                                                    126/247
(Continued)

FOREIGN PATENT DOCUMENTS

CN   203393292 U   1/2014
EP   0 196 449 A1  10/1986
(Continued)

OTHER PUBLICATIONS

Ellis/Kuhnke Controls, Feb. 15, 2015, Benefits and disadvantages of pneumatics.*
(Continued)

*Primary Examiner* — Daniel S Larkin
*Assistant Examiner* — David L Singer
(74) *Attorney, Agent, or Firm* — Oblon, McClelland, Maier & Neustadt, L.L.P.

(57) ABSTRACT

A measuring device for measuring stickiness, imperfections and impurities in textile fibers, such a device includes a housing inside which a pair of rollers are placed, arranged side by side to one another and rotating in opposite senses and between which a web of cotton fibers is made to pass. The rollers are heated, the sticky fractions of the web that adhere to the rollers after the passage of the web between them are detected, and the sticky fractions adhering to the rollers are removed, wherein the heating is controlled by a processing and control unit as a function of the temperature of the rollers detected by a temperature sensor associated with them.

9 Claims, 15 Drawing Sheets

(51) Int. Cl.
  *D01G 31/00* (2006.01)
  *G01N 21/89* (2006.01)
  *G01N 33/36* (2006.01)
  *G01N 21/898* (2006.01)
  *G01N 22/04* (2006.01)
  *G01L 13/00* (2006.01)

(52) U.S. Cl.
  CPC ..... *G01N 21/8915* (2013.01); *G01N 21/8983* (2013.01); *G01L 5/009* (2013.01); *G01L 13/00* (2013.01); *G01N 3/00* (2013.01); *G01N 22/04* (2013.01); *G01N 2203/0282* (2013.01)

(58) Field of Classification Search
  USPC ........... 73/159, 160, 863.91, 863.92, 863.11, 73/863.12, 866, 432.1, 865.8; 700/142, 700/143; 19/66 CC
  See application file for complete search history.

(56) References Cited

U.S. PATENT DOCUMENTS

| | | | | |
|---|---|---|---|---|
| 4,099,297 A | * | 7/1978 | Hasegawa | D01G 23/06 19/240 |
| 4,590,647 A | * | 5/1986 | Fahmuller | D06B 23/30 19/262 |
| 4,796,334 A | | 1/1989 | Yecheskel et al. | |
| 4,888,856 A | | 12/1989 | Yescheskel et al. | |
| 4,969,234 A | | 11/1990 | Waeber et al. | |
| 4,989,297 A | | 2/1991 | Yecheskel et al. | |
| 5,003,670 A | | 4/1991 | Waeber et al. | |
| 5,130,559 A | * | 7/1992 | Leifeld | D01G 31/003 19/65 A |
| 5,153,968 A | * | 10/1992 | Sterin | D01G 99/00 19/200 |
| 5,228,171 A | * | 7/1993 | Leifeld | D01G 23/02 19/105 |
| 5,257,438 A | * | 11/1993 | Faas | D01G 23/04 19/105 |
| 5,636,546 A | * | 6/1997 | Frydrych | D01G 31/00 374/51 |
| 5,700,961 A | * | 12/1997 | Anthony | G01N 33/362 250/339.1 |
| 5,752,294 A | * | 5/1998 | Mor | D01G 31/00 19/66 CC |
| 5,892,142 A | * | 4/1999 | Ghorashi | G01N 33/362 73/38 |
| 6,185,787 B1 | * | 2/2001 | Waeber | D01G 15/24 19/105 |
| 7,451,526 B2 | * | 11/2008 | Duda | D01G 15/46 19/240 |
| 2002/0083764 A1 | * | 7/2002 | Hequet | G01N 33/362 73/159 |
| 2002/0152583 A1 | * | 10/2002 | Bischofberger | D01G 31/006 19/98 |
| 2002/0166211 A1 | | 11/2002 | Farber et al. | |
| 2009/0000068 A1 | * | 1/2009 | Saeger | D01G 15/40 19/115 R |

FOREIGN PATENT DOCUMENTS

| | | | | |
|---|---|---|---|---|
| EP | 1016742 A1 | * | 7/2000 | ............ D01G 19/22 |
| EP | 1659402 A2 | * | 5/2006 | ............ G10N 19/08 |
| GB | 2 375 355 | | 11/2002 | |
| WO | WO 93/23752 | | 11/1993 | |

OTHER PUBLICATIONS

Electronic-Tutorials.ws, May 9, 2013, Electronics Tutorial about a Closed Loop Systems.*
Italian Search Report dated May 11, 2016 in Italian Application UB20155249, filed on Oct. 30, 2015 ( with English Translation of Categories of Cited Documents).

* cited by examiner

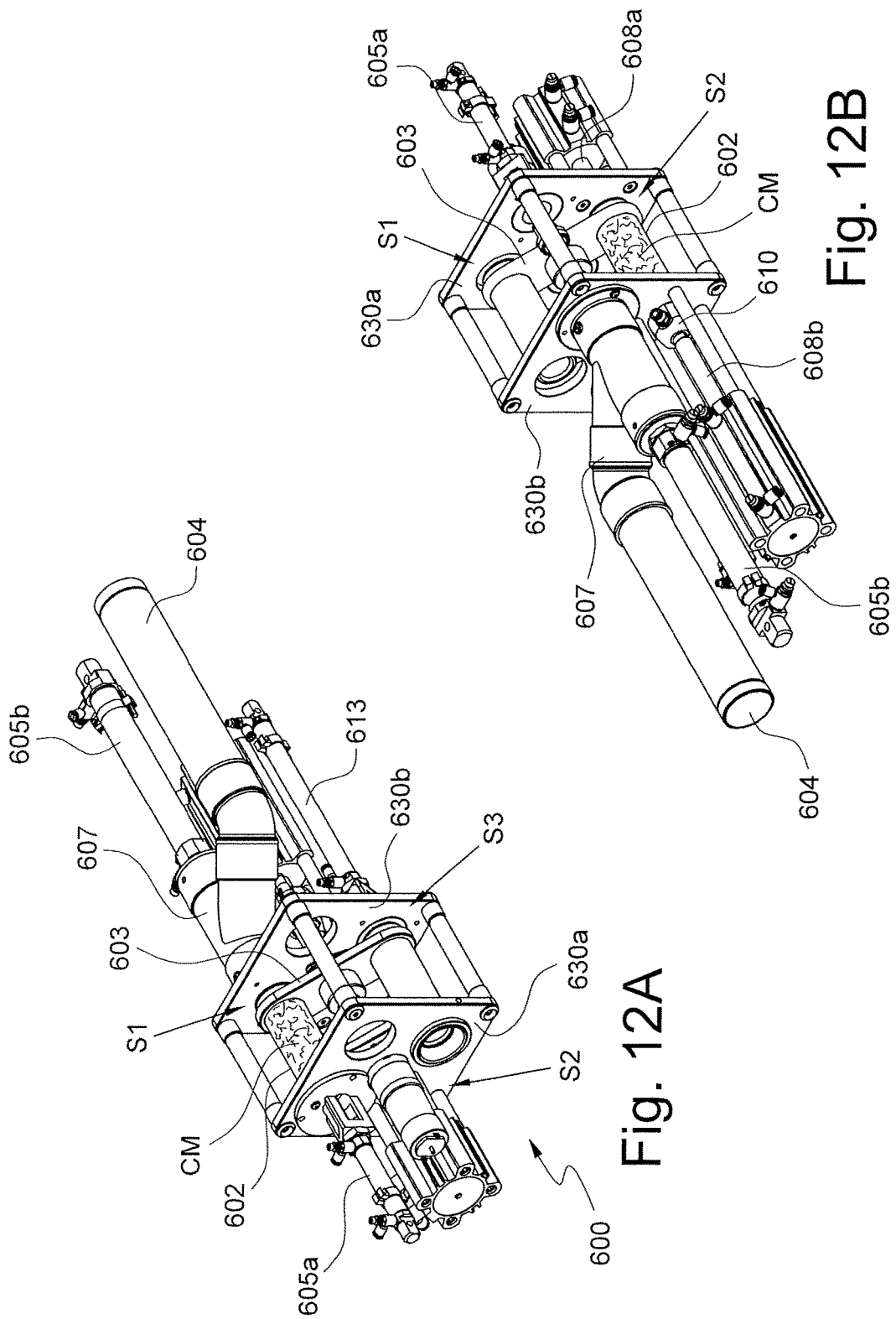

MEASURING DEVICE FOR MEASURING THE STICKINESS, IMPERFECTIONS AND IMPURITIES OF TEXTILE FIBERS, IN PARTICULAR COTTON FIBERS

The present invention refers to a measuring device for measuring the cotton stickiness, imperfections and impurities of textile fibers, in particular cotton fibers.

Devices of this type are for example known from U.S. Pat. No. 5,752,294 and are used as independent apparatuses or as modules integrated in modular apparatuses structured and configured to carry out a plurality of measurements of a plurality of characteristics adapted to qualify the cotton fibers according to criteria defined by classifications recognized at national ox international level.

In known devices, the stickiness of cotton fibers, which is due to physiological, structural, cultivation and harvesting factors, is measured by making a web of fibers advance between a pair of rollers heated to a temperature such as to promote the adhesion on their outer side surface of the sticky fractions of the fibers. The rollers are generally heated to a temperature close to 38-40° C., which has been experimentally found to be the best for overcoming the problems that generate during the carding step, although the latter is carried out at room temperature.

Downstream of such rollers detection means are arranged, for example of the optical type and, in particular, of the laser type, for detecting the sticky fractions still adhering to the outer side surface of the rollers.

Moreover, removal weans, are provided, which are adapted to remove from the outer side surface of the rollers the sticky fractions adhering thereto, before said outer side surface encounters again the web dragged between the rollers.

In order for the sticky fractions of the cotton fibers to adhere to the outer side surface of the rollers, it is necessary for the latter to be heated and kept at a temperature such as to promote such adhesion.

In known devices, the outer side surface of the rollers is heated by friction action exerted on it by rotating brushes placed in contact with it.

As a function of the distance that exists between the outer side surface of the rollers and the respective brush, the friction action and therefore the degree of heating of the rollers varies.

In known devices, this distance is pre-set manually by assigned operators and adjusted, still manually, during the course of tests in order to try to keep the temperature of the rollers substantially constant. These and other purposes of the present invention are accomplished with a measuring device for measuring the cotton stickiness, imperfections and impurities of textile fibers, in particular cotton fibers.

It is thus clear that such adjustment requires the intervention of workers and depends on the experience and sensitivity of the single operators, since substantial fluctuations of the temperature of the rollers often, occur, which affect the execution of tests and their results.

The purpose of the present invention is to avoid the drawbacks of the prior art.

In this general purpose, a particular purpose of the present invention is to propose a measuring device for measuring the cotton stickiness, imperfections and impurities of textile fibers, in particular cotton fibers, which allows carrying out the measurements in stable test conditions and obtaining precise and reliable measurements.

Another purpose of the present invention is to provide a measuring device for measuring the cotton stickiness, imperfections and impurities of textile fibers, in particular cotton fibers, which is structurally and constructively simple and is cost effective and that can be used as an independent apparatus or integrated as a module in a modular apparatus structured and configured to carry out measurements of a plurality of characteristics of cotton fibers.

These and other purposes of the present invention are accomplished with a measuring device for measuring the cotton stickiness, imperfections and impurities of textile fibers, in particular cotton fibers, as outlined in claim 1.

Further characteristics are specified in the dependent claims.

The characteristics and advantages of a measuring device for measuring cotton stickiness, imperfections and impurities of textile fibers, in particular cotton fibers, according to the present invention will become clearer from the following description, given as an example and not for limiting purposes, referring to the attached schematic drawings, in which:

FIGS. 12A to 12C show axonometric views of a further module of the apparatus of FIGS. 1 and 2 comprising a measuring device for measuring the fineness and maturity of the textile fibers, in particular cotton fibers, in successive operative positions;

Figure 1:
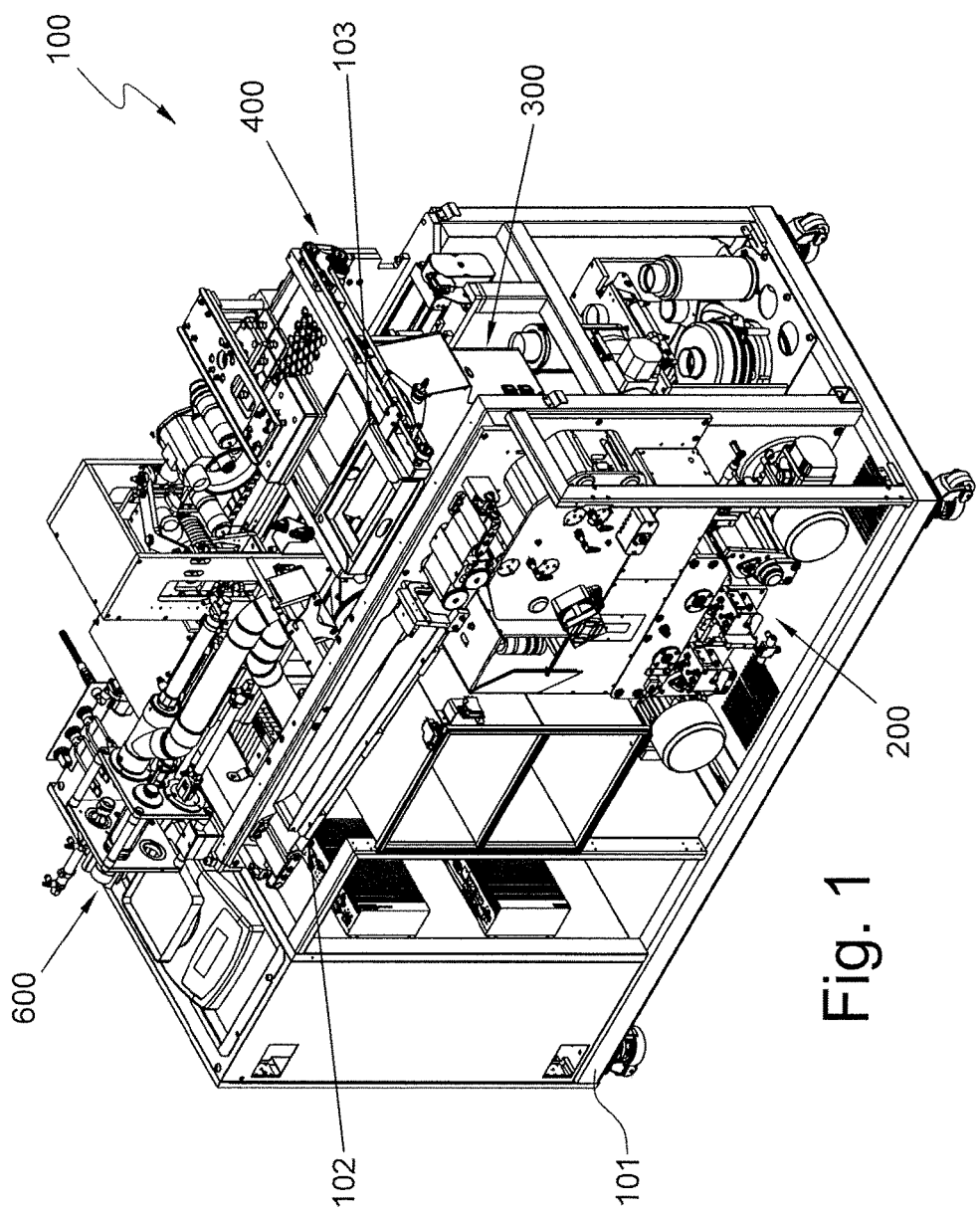
FIGS. 1 and 2 are schematic and axonometric views of a modular apparatus for measuring characteristics of cotton fibers, in which one of the measuring modules consists of the measuring device according to the present invention.
Figure 2:
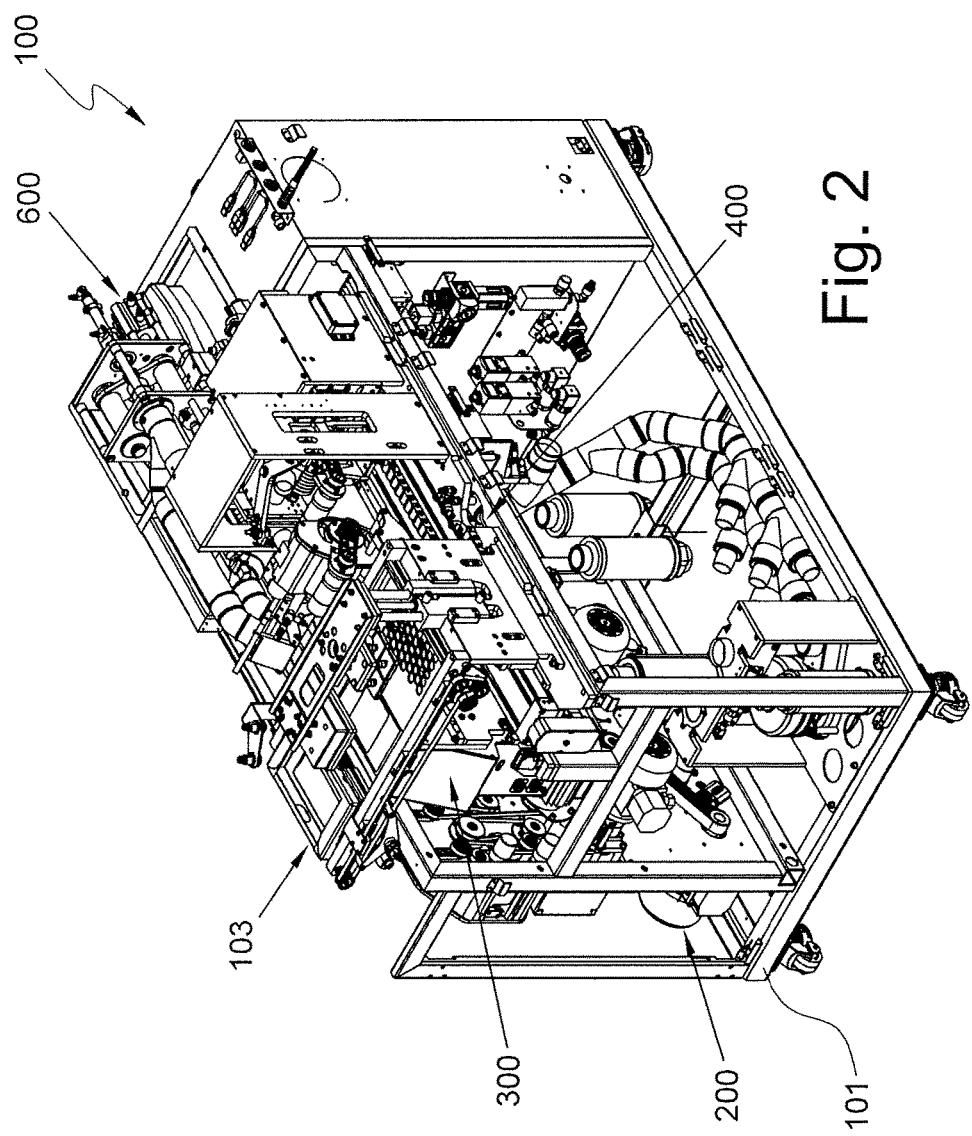
Figure 3:
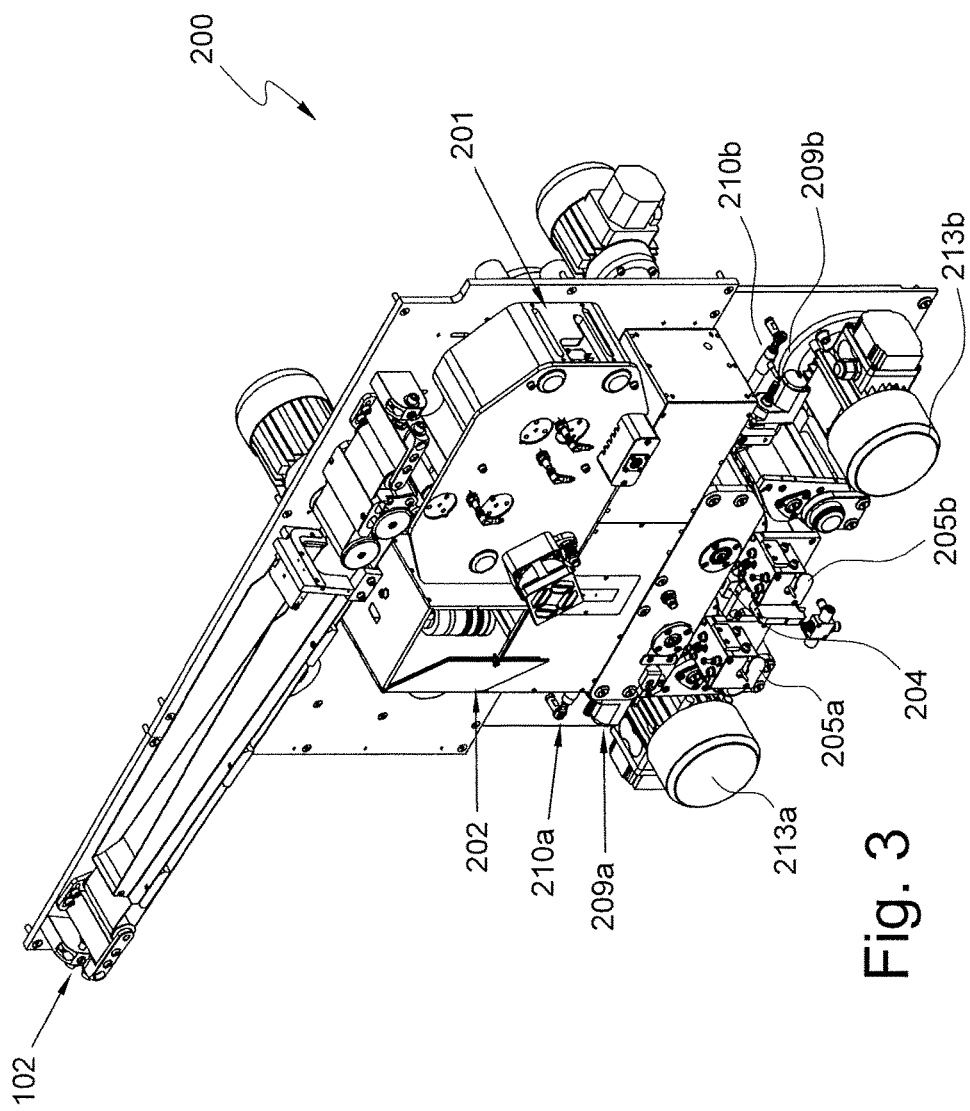
FIG. 3 is an axonometric view of the module of the apparatus of FIG. 1 consisting of the measuring device according to the present invention.

With reference to the attached figures, a modular apparatus for measuring a plurality of characteristics of textile fibers, in particular cotton fibers, is wholly indicated with 100.

Hereinafter reference will be made, for the sake of simplicity, to fibers, meaning textile fibers and in particular textile fibers of plant origin and even more specifically cotton fibers.

The apparatus 100 comprises a support structure 101 that supports a plurality of modules, each comprising at least one measuring device for measuring at least one characteristic of the textile fibers and a central control and operating unit for controlling and operating such modules, not shown since they are of the type known to the person skilled in the art.

In the embodiment represented in the attached figures, the apparatus 100 comprises:

a first module comprising a measuring device 200 for measuring the cotton stickiness and imperfections, such as knots or tangles of fibers ("neps"), and/or impurities, such as residues of insects, seed fragments or other, present in the fibers, according to the present invention, a second module comprising a measuring device 300 for measuring the color and detecting impurities in the cotton fibers, a third module comprising a measuring device 400 for measuring the moisture content, the length and at least one dynamometric characteristic selected from the group comprising elongation under tension before breaking and tensile strength (i.e. the maximum stress under tension before breaking), a fourth module comprising a measuring device 600 for measuring the fineness and maturity of the fibers.

The apparatus 100 is provided with two inlet devices for inletting a respective sample of fibers to be tested:

a first inlet device 102, of the conveyor belt type, for inletting a first sample and that feeds the measuring device 200 for measuring the stickiness and imperfections and/or impurities, and a second inlet device 103, of the movable drawer type, for inletting a second sample and that feeds in succession the measuring device 300 for measuring the color and for detecting impurities and the measuring device 400 for measuring the moisture content, the length and the dynamometric characteristics of the fibers, the measuring device 600 for measuring the fineness and maturity of fibers is fed with the fibers exiting from the measuring device 200 for measuring the stickiness, which are sucked and fed to the measuring device 600 for measuring the fineness and maturity.

Each module can be equipped with an own microprocessor or electronic processing and control unit in turn integrated or connected to the central electronic processing and control unit, or it can be directly controlled and operated by the latter. The apparatus 100 is provided, in particular, with two control and operating units respectively configured for automatically managing the various modules of which it consists and for processing the data collected by them.

The measuring device 200 for measuring the stickiness, imperfections and/or impurities of fibers is, in general terms, of the type described in U.S. Pat. No. 5,752,294.

Such a measuring device 200 is fed with a mass of fibers by the first, inlet device 102 and comprises, arranged in succession to one another:

card means 201 that receive at the inlet the mass of fibers fed by the first inlet device 102 and that are adapted for preparing- and forming, in a known way, a web of fibers, acquisition means 202 for acquiring images of the web exiting from the card means 201, a pair of rollers 203a, 203b side by side to one another and counter-rotating and configured for measuring the stickiness, means 204 for dragging the web advancing along the path defined by the card means 201, by the acquisition means 202 and by the pair of rollers 203a, 203b.

The card means 201 comprise a plurality of cards that are not described in detail, since they are of the type known to the person skilled in the art.

The acquisition means 202 comprise a space inside which, for example, a video camera or other optical sensor, one or more contrast screens and/or devices for illuminating the web are arranged. Such acquisition means 202 are connected to processing means configured to detect the presence of imperfections and/or impurities and possibly the shape and color of such imperfections and/or impurities. Advantageously, the video camera is of the color type and operates in combination with a first illuminating group and/or with a second illuminating, group of the web, which groups face one another. This allows detecting and determining the type of the impurities present, whether they are plant fragments (grasses or seed shells), insect fragments or fragments of artificial fibers like, for example, polymeric fibers (polyethylene) deriving from bags and ties.

Also in this case, the acquisition means 202 are not described any further, being of the type that can be immediately understood by the person skilled in the art.

Each roller 203a, 203b is associated with heating means adapted for heating at least the outer side surface of the roller 203a, 203b that contacts the web so as to promote the adhesion thereto of the sticky fractions of the fibers, detection means 205a, 205b for detecting the sticky fractions of the web adhering to the roller 203a, 203b following the passage of the web, and removal means 206a, 206b for removing the sticky fractions from the roller 203a, 203b.

The measuring device 200 is also provided with an electronic processing and control unit that is not shown in the attached figures, since it is of the type known to the person skilled in the art. Such an electronic processing and control unit is advantageously of the programmable type and is connected or in any case integrated to the central electronic processing and control unit of the apparatus 100.

According to the present invention, the operation of the heating means is controlled by the electronic processing and control unit as a function of the temperature of the rollers 203a, 203b detected by temperature sensor means 207a, 207b (i.e. temperature probes) associated with them. In greater detail, the heating means comprise for each roller 203a:

at least one contact body 208a, 208b that is guided in a movable manner towards and away from the outer side surface of the respective roller 203a, 203b to exert a friction action on it such as to promote the heating thereof, and actuator means 209a, 209b for actuating the movement of such a contact body 208a, 208b towards and away from the respective roller 203a, 203b, wherein the electronic processing and control unit is adapted to control the actuator means 209a, 209b as a function of the signals emitted by the temperature sensor means 207a, 207b in order to vary the position of the respective contact body 208a, 208b with respect to the corresponding roller 203a, 203b.

Advantageously, moreover, position sensor means 210a, 210b are also provided for detecting the position of the actuator means 209a, 209b, said position sensor means 210a, 210b are connected to the electronic processing and control unit, wherein the electronic processing and control unit is adapted to control and operate the actuator mesas 209a, 209b as a function of the signals emitted by the temperature sensor means 207a, 207b and by the position sensor means 210a, 210b.

Each contact body 208a, 208b consists of a brush roller that is supported in a rotating manner by a support bracket 211a, 211b.

Each support bracket 211a, 211b has a first portion that is coupled to the housing 101 or in any case to the housing of the measuring device 200 in a rotating manner about an axis B parallel to the axis of the respective brush roller and a second portion that is articulated to the actuator means 209a, 209b. The actuator means 205a, 205b are preferably of the linear type and, in the embodiment shown, comprise a screw-nut screw pair the nut screw of which is driven in rotation by an electric motor and the screw of which has an end articulated to the respective support bracket 211a, 211b.

The position sensor means 210a, 210b consist of linear transducers associated with the screw of the respective actuator means 209a, 209b.

Each contact body 208a, 208b formed by a brush roller is driven in rotation by own respective motor means 213a, 213b controlled and operated by the electronic processing and control unit. As a function of the signals emitted by the temperature sensor means 207a, 207b and by the position sensor means 210a, 210b, the electronic processing and control unit controls and operates the actuator means 209a, 209b in order to modify the position of the contact bodies 208a, 208b with respect to the rollers 203a, 203b so as to modify the friction action exerted by the first on the outer side surface of the second and, consequently, the temperature reached by said outer side surface so as to keep it close to a preset value (generally about 38-40° C.) and suitable for the sticky fractions of the web passing between the rollers 203a, 203b to adher onto it.

It is thus possible for the temperature of the rollers 203a, 203b to reach and maintain a preset value without the possibility of errors, reducing the possible transient times.

According to a further aspect of the present invention, at least one of the two rollers 203a, 203b is supported in a movable, manner towards and away from the other along a direction orthogonal to their longitudinal axes and is coupled to actuator means for actuating such movement. Pressure sensors are also provided, which are configured to detect, directly or indirectly, the contact pressure between the two rollers 203a, 203b. These sensors are, for example force sensors configured to detect the force exerted by the actuator means acting on the movable roller or to detect the load acting on the support shafts of the two rollers. The electronic processing and control unit, whether it is local or central, is configured to operate the actuator means for actuating the mutual movement of the two rollers as a function of the signals detected by the pressure sensors so as to keep the contact pressure between the two rollers substantially constant and close to a preset value. The degree of stickiness, in fact, as known, also depends on the pressure that the two counter-rotating rollers exert on the web of fibers.

The detection means 205a, 205b are of the laser type and are not described any further, since they are of the type known to the person skilled in the art. The signals detected by them are sent and processed by the electronic processing and control unit.

The removal means 206a, 206b consist of the same contact bodies 208a, 208b in the form of brush rollers and rotating at greater angular speeds than those of the respective rollers 203a, 203b and of a brush or knife 212a, 212b. Also in this case, the removal means 206a, 206b are not described any further, being of the type known to the person skilled in the art and being able to have different embodiments.

The dragging means 204 are of the suction (depression) type and are configured to exert a sufficient action on the web to allow it to advance along the path downstream of the card means 201 and along the image acquisition means 202 and the pair of rollers 203a, 203b without however impeding the adhesion of the sticky fractions to the rollers 203a, 203b themselves.

For the sake of completeness, the remaining measuring devices forming the remaining modules of the apparatus 100 will now be described, some of which are the object of a separate patent application to the same applicant. In any case, it is specified that each of such measuring devices can be made as an independent apparatus or integrated with one or more of the other measuring devices in a modular apparatus of the type of the apparatus 100 shown in FIG. 1.

FIGS. 7 to 10 show the measuring device 400 for measuring the moisture content, the length and/or the dynamometric characteristics of the fibers that is arranged in succession to the measuring device 300 for measuring the color and detecting impurities of the fibers forming a same sample fed by the second inlet device 103.

The second inlet device 103 is of the drawer type 104, which is filled with fibers and is guided in a movable manner along a path that crosses the measuring device 300 and that introduces the sample into the measuring device 400.

The drawer 104 consists of a frame; the opposite faces of the drawer 104 that are parallel to the sliding plane of the drawer itself are open.

The measuring device 300 comprises, in a known way, a table 301 on which the drawer 104 is made to slide.

The table 301 comprises a sheet 302 of material that is transparent to light below which a space 303 is obtained containing optical analysis devices for the optical analysis of the fibers of the sample contained in the drawer 104. Such optical analysis devices comprise, for example, a video camera 304 advantageously in color and/or a spectrophotometer 305 and allow detecting the degree of color of the fibers and the presence of impurities in them, like for example insect and/or plant residues (like seed fragments).

The measuring device 400 is arranged in succession to the measuring device 300, such two devices being able to be integrated in a unique module.

The measuring device 400 comprises a housing 401 that is integrated in the support structure 101 and in which two areas are defined:

a preparation area ZP for preparing a line or "beard" of fibers arranged substantially parallel and coplanar to each other and a measuring area ZM in which the fibers forming the line or "beard" are subjected to the measurements of length and/or of the dynamometric characteristics and advantageously both such measurements in succession.

Figure 4:
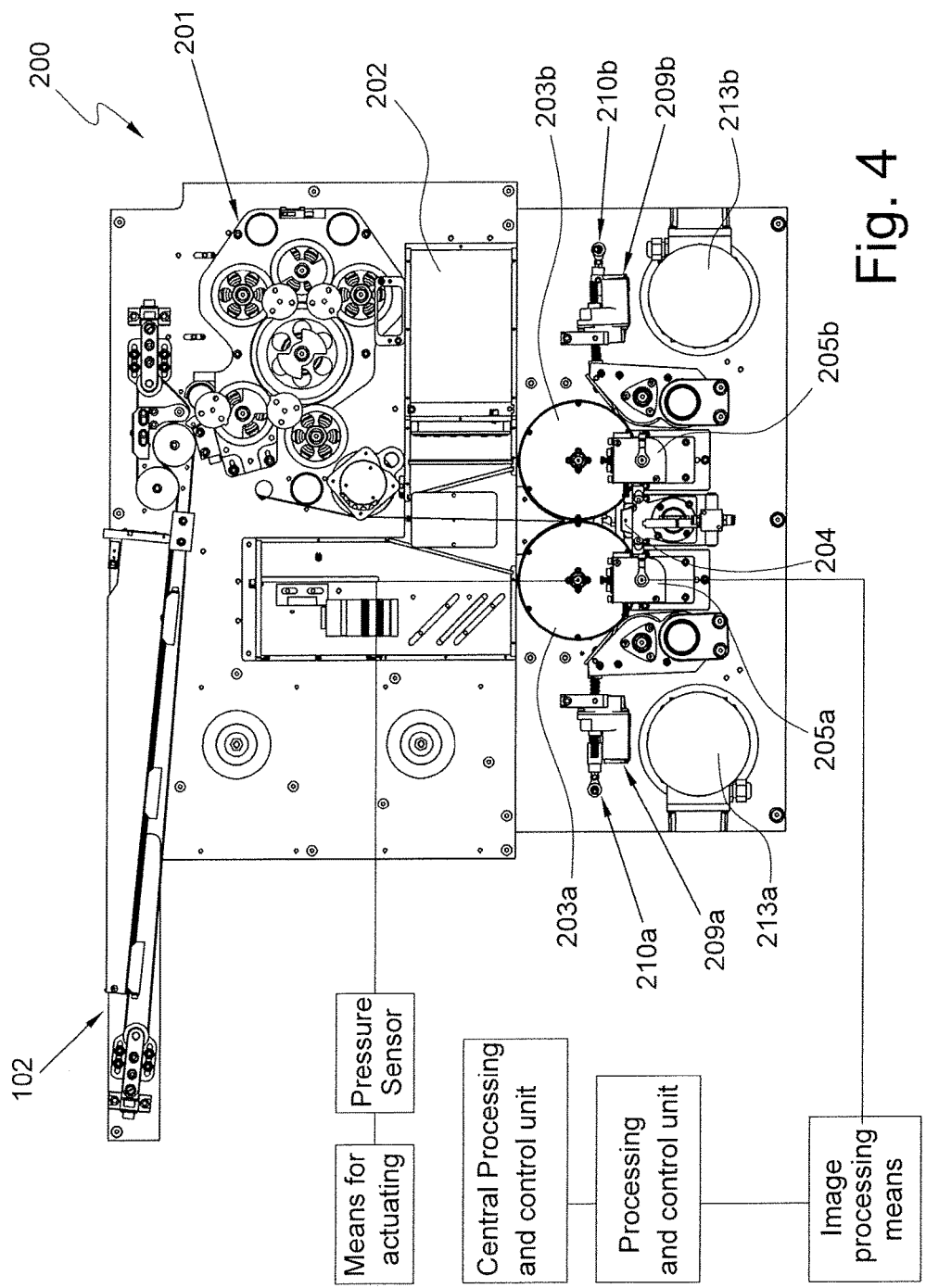
FIG. 4 is a schematic front view of the measuring device of FIG. 3 with some covers removed.
Figure 5:
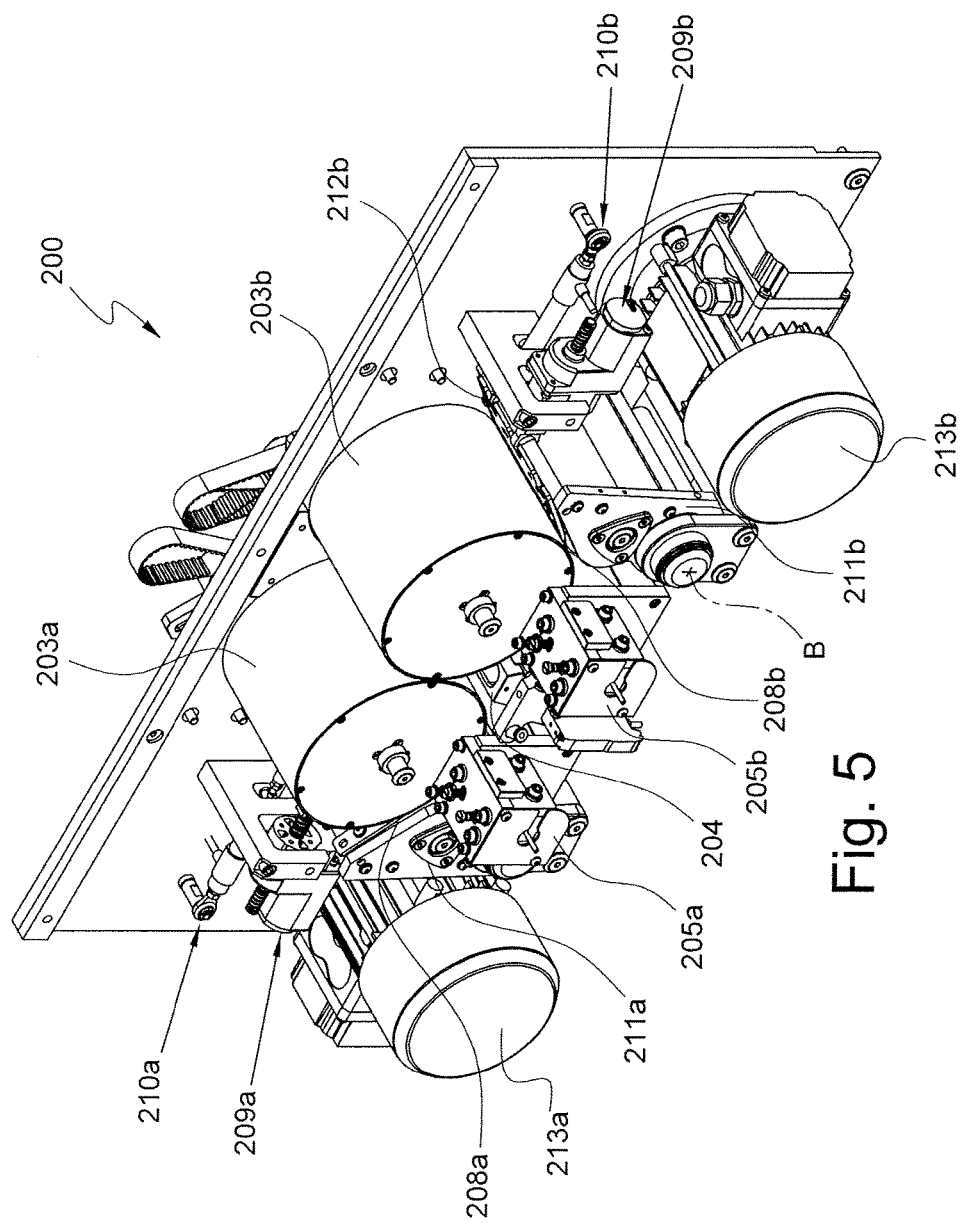
FIG. 5 shows a detail of FIG. 3 on an enlarged scale.
Figure 6:
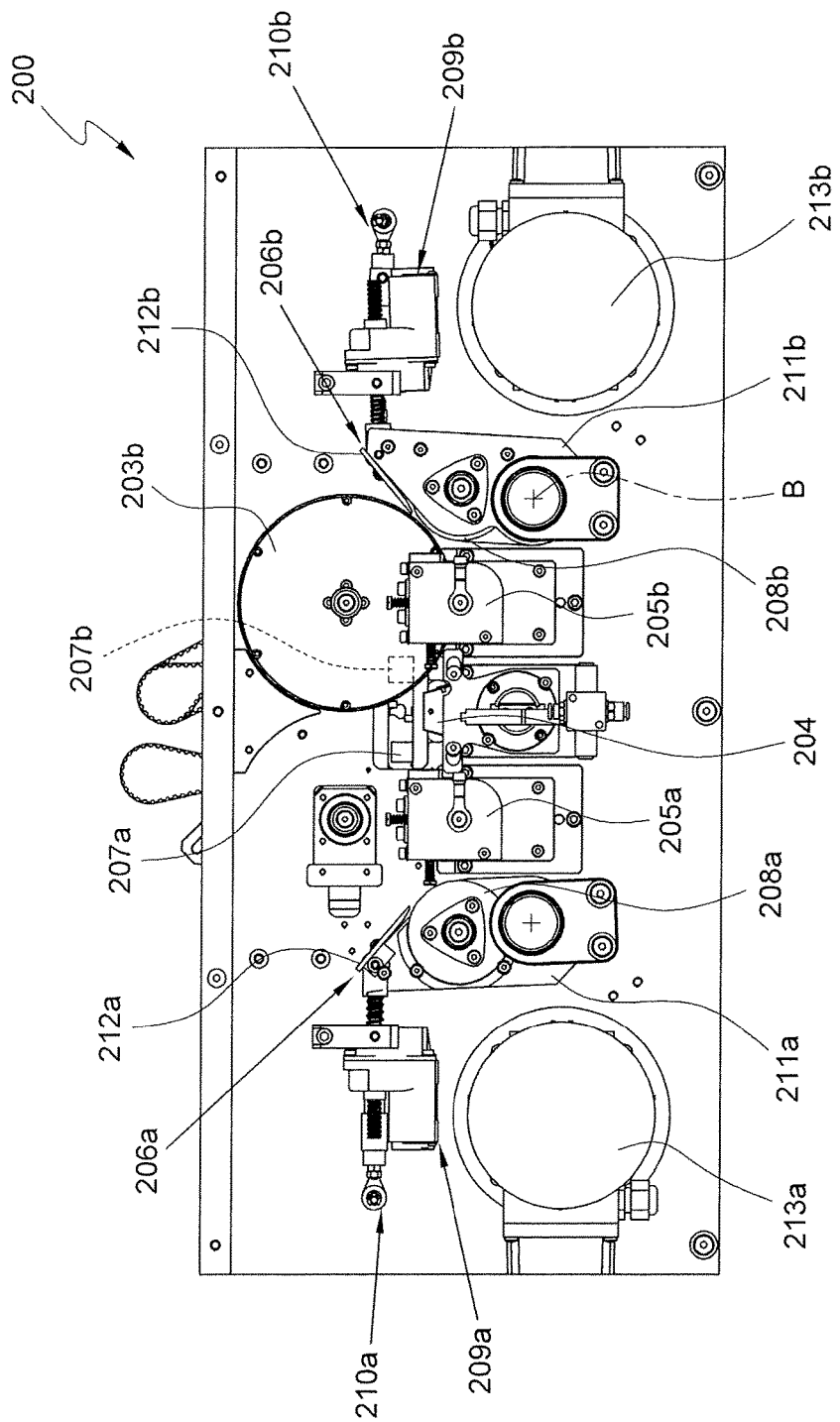
FIG. 6 is a front view of FIG. 5 with some parts removed.
Figure 7:
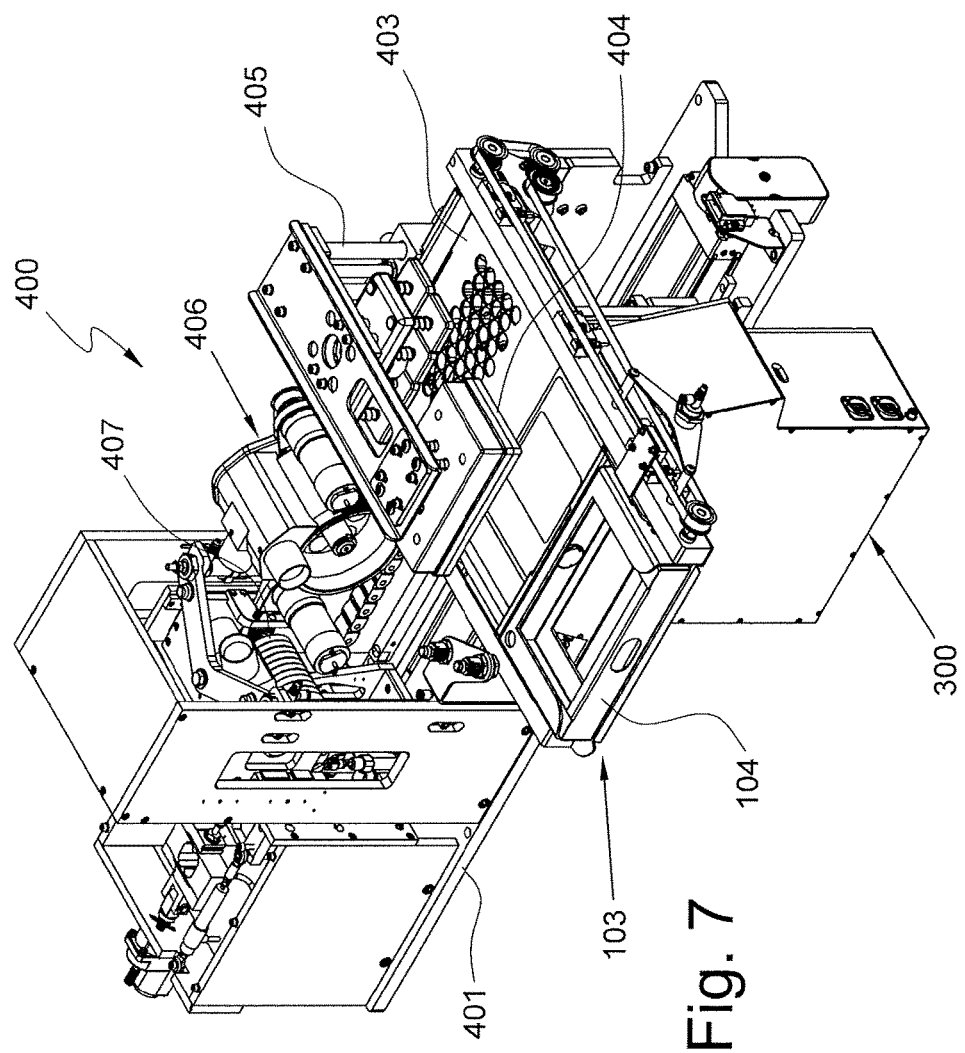
FIG. 7 is a schematic and axonometric view of a further module of the apparatus of FIGS. 1 and 2, comprising a measuring device for measuring the moisture content, the length and the dynamometric characteristics of cotton fibers.

The line or "beard" of fibers is handled and transported between the preparation area ZP and the measuring area ZM by a metallic comb 402, which is associated with the housing 401 in a movable manner with the possibility of carrying out both translation movements and rotation movements, schematically illustrated in FIG. 4.

The preparation area ZP comprises:

a grid or in any case a perforated plate 403 arranged along the sliding path of the drawer 104 in succession to the table 301 and coplanar to it, a pressure plate 404 that is arranged above the perforated plate 403 and that is substantially parallel to it and that is supported in a movable manner towards and away from the perforated plate 403 along a direction orthogonal thereto, linear actuator means 405 for actuating the sliding of the pressure plate 404, card means 406, brush means 407 and suction means arranged in succession beside the "press" formed by the perforated plate 403 and the pressure plate 404.

Advantageously, the linear actuator means 405 are of the pneumatic cylinder-piston type and comprise a proportional pressure regulator configured and operated to keep the pressure of the operating fluid substantially equal to a preset value, so as to ensure that the layer of sample interposed between the pressure plate 404 and the perforated plate 403 is pressed at known predetermined conditions.

The comb 402 is coupled with a jaw element 408, which is movable between a closed position and an open position. The comb 402 with the coupled jaw element 408 is supported by a head mounted on a bracket; the bracket is movable in a sliding manner along a rectilinear guide 409 and is actuated along such a rectilinear guide 409 by a linear actuator (of the type for example of a recirculating ball screw-nut screw coupling actuated by a motor) by means of which it, and with it the comb 402 and the jaw element 408, is moved along the preparation area ZP and towards the measuring area ZM. The head that supports the comb 402 and the jaw element 408 coupled to it is also rotatable about a horizontal axis (parallel to the perforated plate 403) orthogonal to the direction defined by the rectilinear guide 409.

The comb 402 is adapted for hooking the fibers forming a line or "beard".

In a known way, the drawer 104 is made to slide so as to position above the perforated plate 403. The pressure plate 404 is brought close to the perforated plate 403 and pressed onto it by means of the actuator means 405, the sample of fibers interposed between the two plates forms a pressed layer that forms protuberances that project from the openings of the perforated plate 403 at the lower face thereof (i.e. the face of the plate 403 opposite the one facing the pressure plate 404).

Advantageously, the proportional pressure regulator allows applying to the layer of fibers a constant pressure equal to a preset value; the compacting degree of the pressed layer and the entity of the protuberances thereof projecting from the perforated plate 403 in fact depends on such a value.

The comb 402 is brought below the perforated plate 403 to pick up a line of fibers from the protuberances formed by the layer pressed against the perforated plate 403 itself.

The comb 402 is then translated in succession first at the card 406 that eliminates the exceeding fibers from the line or "beard" and then at the brush 407 that parallelizes the fibers of the line or "beard". During these steps the comb 402 is arranged with the prongs horizontal and the jaw element 408 is in the open position. The line or "beard" of fibers thus made parallel and substantially coplanar is clamped on the comb 402 by the jaw element 408, rotated in the horizontal position and brought at the inlet to the measuring area ZM.

In the measuring area ZM there are arranged:
measuring means 410 for measuring the length of the fibers forming the line or "beard",
dynamometer means for measuring at least one dynamometric characteristic and that comprise gripper members, which comprise a fixed gripper 411a and a movable gripper 411b towards and away from the fixed gripper 411a, the fixed gripper 411a and the movable gripper 411b clamp two end portions of the line or "beard" of fibers,
detection means (not described in detail, being of the known type) for detecting the relative movement of the movable gripper 411b with respect to the fixed gripper 411a when both the movable and fixed grippers are in the gripping and holding positions of respective portions of the fibers of the line or "beard",
detection means (not described in detail, being of the known type) for detecting the tensile force applied to the fibers of the line or "beard" during the relative movement of the movable gripper 411b with respect to the fixed gripper 411a when both the movable and fixed grippers are in the gripping and holding positions of a respective portion of the fibers forming the line or "beard".

Moreover, extraction means 412 are provided for extracting the textile fibers of the line or "beard" from the measuring area ZM. These extraction means 412 comprise a conduit that has one end in communication with the measuring area ZM and the opposite end associated with suction means adapted to create a depression of an entity such as to draw the fibers and the pieces thereof released by the gripper members at the end of the execution of the dynamometric tests.

The data relating to the relative movement of the movable gripper 411b with respect to the fixed gripper 411a and to the tensile force applied by the movable gripper 411b to the fibers of the line or "beard" are then processed in a known manner in order to obtain dynamometric characteristics of the fibers themselves.

This does not exclude the possibility that the comb 402 can constitute the fixed gripper.

The measuring device 400 comprises measuring means 413 for measuring the moisture content of the fibers forming the layer of fibers pressed between the pressure plate 404 and the perforated plate 403 and/or of the fibers forming the line or "beard", which are respectively arranged in the preparation area ZP and/or in the measuring area ZM and/or are associated with the extraction means 412 to detect the moisture content of the fibers forming the pressed layer and/or the line or "beard" just before and/or just after the execution of the measurement of their length and/or the measurement of their dynamometric characteristics.

In a preferred embodiment the measuring means 413 for measuring the moisture content are arranged at the inlet to the measuring area ZM or at the extraction means 412 to detect the moisture content of the fibers forming the line or "beard" just before and/or just after the execution of the measurement of their length and/or the measurement of their dynamometric characteristics. This allows detecting the moisture content of the same fibers that are then the object of the measurements of length and of the dynamometric characteristics, in times close to the execution of such measurements and substantially under the same environmental conditions in which such measurements are carried out. The values of the length, of the dynamometric characteristics and of the moisture content can thus be correlated with each other with good margins of certainty.

These measuring means 413 for measuring the moisture content are of the microwave type and comprise one or more microwave sensors.

The use of microwave sensors allows obtaining precise measurements, affected by negligible errors and independent from the degree of distribution of the moisture in the fibers.

Sensors of this type consist, for example, of the microwave sensors of the firm TEWS ELEKTRONIK GmbH & Co. KG.

Such microwave sensors can be of the planar type, of the "fork" type, i.e. consisting of two cylinder means facing one another and between which a microwave field is generated, or of the tubular type.

Figure 8:
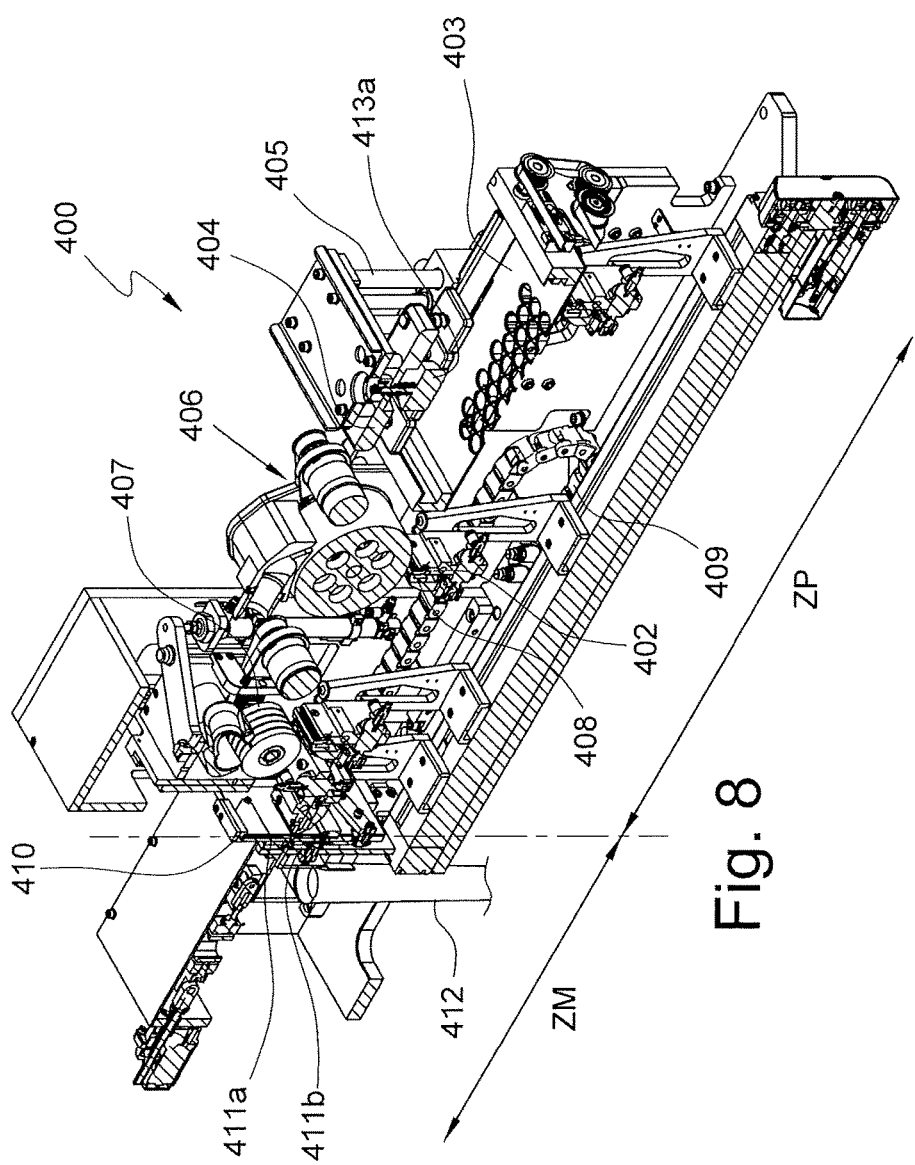
FIG. 8 is a schematic section view of FIG. 7.
Figure 9A:
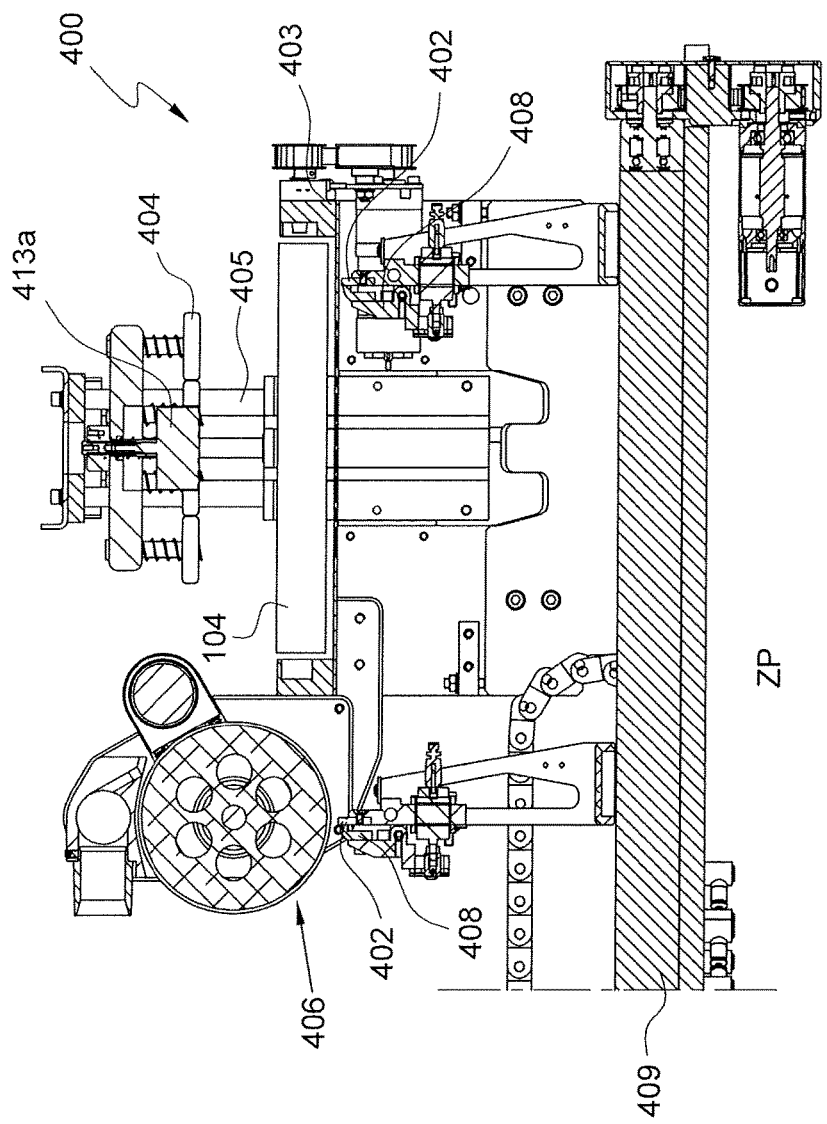
FIGS. 9A and 9B are schematic section views of a respective detail of FIG. 8.
Figure 9B:
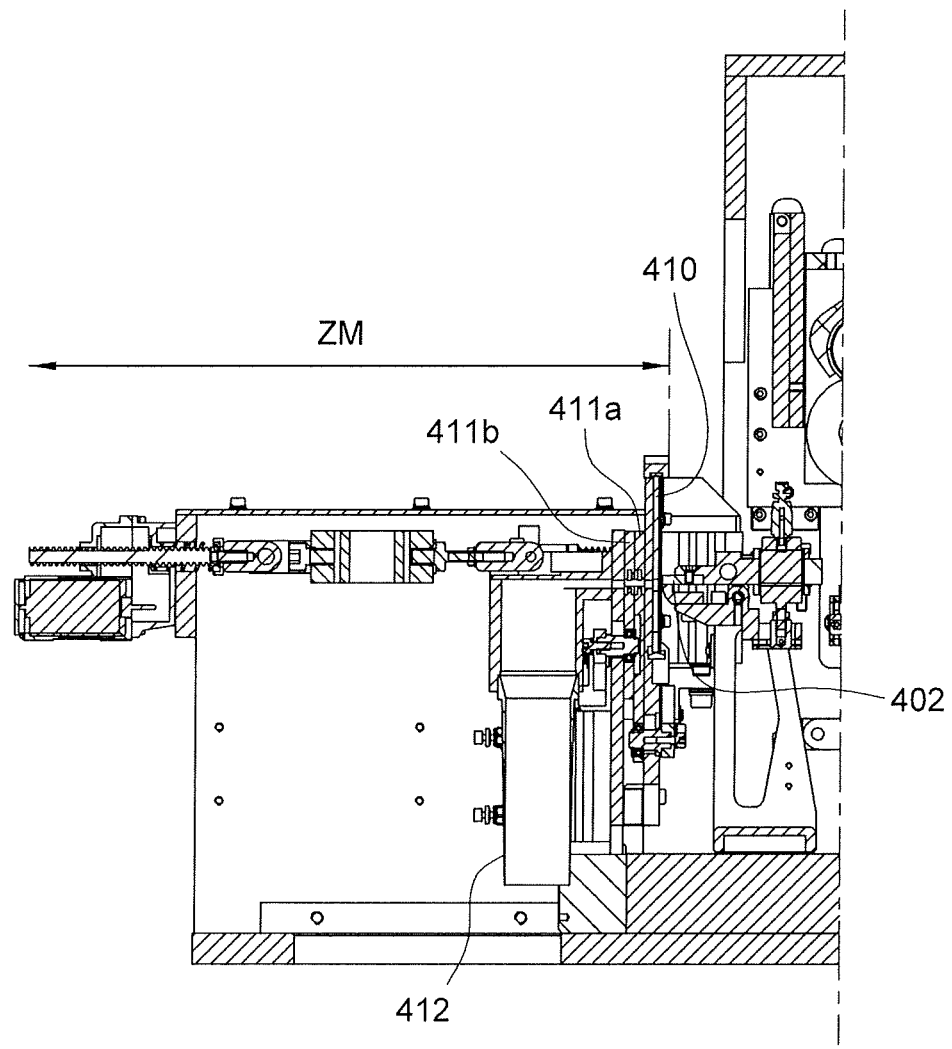

For example, in a possible embodiment represented in FIGS. 8 and 9A, the measuring means 413 for measuring the moisture content are arranged at the preparation, area ZP and comprise a microwave sensor 413. A of the planar type supported by the pressure plate 404. Such a microwave sensor 413A is brought into contact with the layer of fibers pressed between, the pressure plate 404 and the perforated plate 403 to detect the moisture content of the fibers forming the layer.

Figure 10:
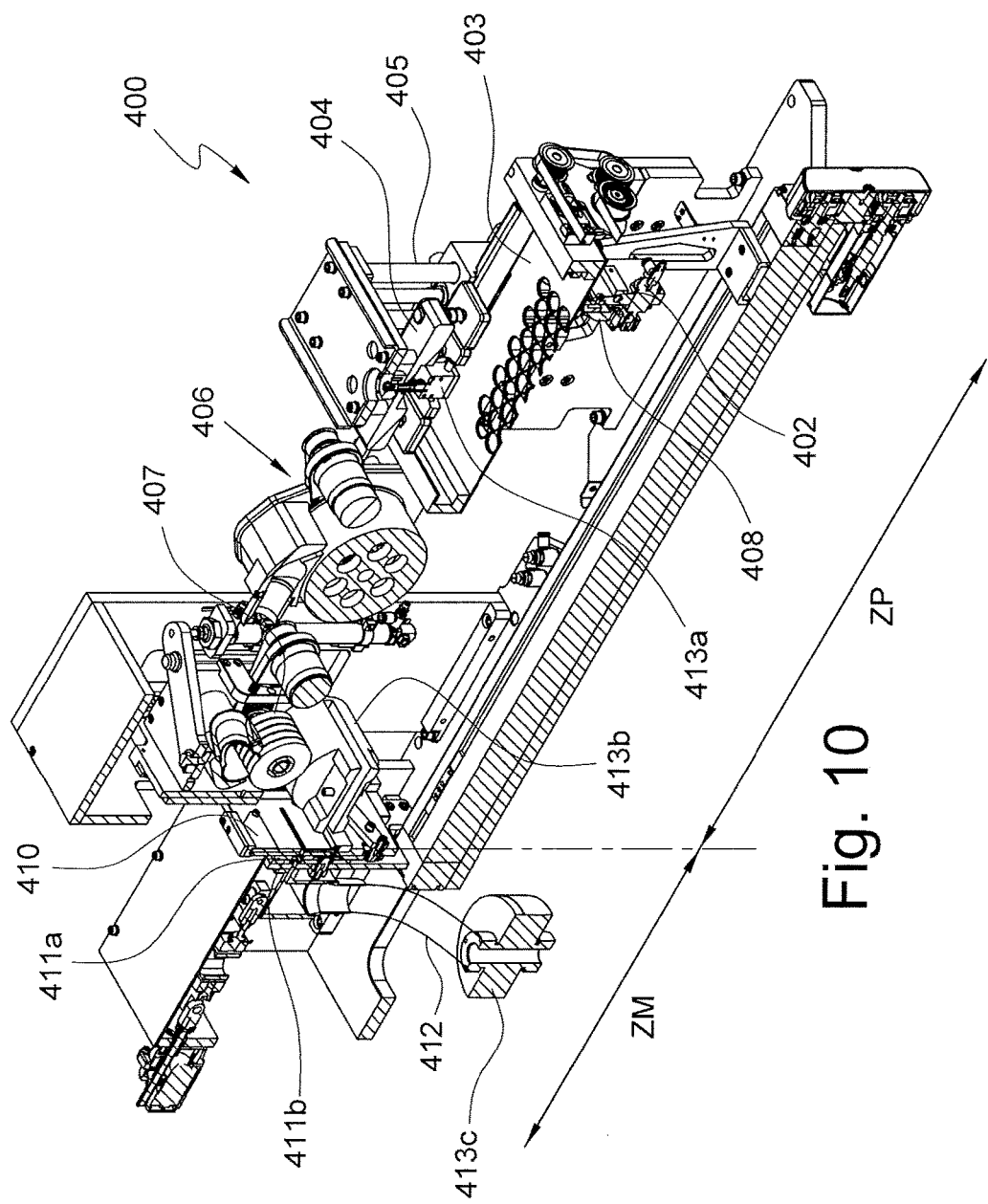
FIG. 10 is a view like that of FIG. 8 showing different possible embodiments of the measuring device for measuring the moisture of the fibers.

Alternatively or in addition, the measuring means 413 for measuring the moisture content of the fibers comprise a microwave sensor 413B of the "fork" or double type for measuring the moisture content of the fibers forming the line or "beard" before the measurement of their length or after the measurement of their length and before the measurement of their dynamometric characteristics. With reference to FIG. 10, such a microwave sensor 413B of the "fork" type is arranged at the inlet or the measuring area ZM.

Alternatively or in addition, the measuring means 413 for measuring the moisture content of the fibers comprise a microwave sensor 413C of the tubular type arranged along the conduit, of the extraction means 412.

In this last case, the measurement of the moisture content is carried out on the fibers or on the pieces of fibers released by the gripper members after the execution of the dynamometric tests and along the path of the fibers moving away from the measuring area ZM.

With reference to FIGS. 12A to 12C and 13 the measuring device 600 for measuring the fineness and maturity of the fibers is now described, which operates according to known air flow methods.

As known, mature cotton fibers have a hollow cross section and are in the form of a flattened floss the inside of which consists of is solid part (cell wall) of cellulose that delimits a hollow part (lumen). Generally, the measurement of the fineness/maturity of cotton fibers obtained with air flow methods is accompanied by the so-called combined fineness and maturity index known in the field as Micronaire.

As stated above, the measuring device 600 operates with an air flow method, in which a known quantity of fibers is enclosed inside a measuring chamber of known dimensions and crossed by an air flow, the fineness and the maturity of the fibers being determined indirectly from the losses of pressure across the measuring chamber due to the resistance that the fibers exert on the air flow that passes through the measuring chamber itself. Such a measuring device 600 can operate at constant pressure or at constant flow.

The measuring device 600 comprises a support frame 601 on which a measuring chamber CM is mounted, said chamber being formed from a hollow cylinder 602 the axially opposite ends of which are open. The hollow cylinder 602 is mounted on the frame 601 in a movable manner between an insertion station S1, at which a known sample of fibers is inserted into the measuring chamber CM, a measuring station S2, at which the measurements are carried out on the sample inserted inside the measuring chamber CM, and an extraction station S3, at which, at the end of the measurements, the sample of fibers is extracted from the measuring chamber CM. In the embodiment represented in the attached figures, the hollow cylinder 602 is mounted on a carousel 603 rotatable about a rotation axis, the insertion station S1, the measuring station S2 and the extraction station S3 being defined along the circular path followed by the hollow cylinder 602. The carousel 603 is mounted between a pair of plates 630a and 630b facing one another and parallel and which are crossed by a plurality of openings adapted to be arranged in communication with the open ends of the hollow cylinder 602 and at which the three operative stations S1, S2 and S3 are defined.

The insertion station S1 comprises a supply conduit 604 for feeding the cotton fibers entering the hollow cylinder 602, these cotton fibers are sucked from the outlet of the measuring device 200 for measuring stickiness and can be weighed in advance. The insertion station S1 also comprises a pair of first pistons that are aligned with and opposite each other and can be inserted into the opposite ends of the hollow cylinder 602. These first pistons are actuated by a respective first linear actuator 605a, 605b between a position extended into the hollow cylinder 602 in order to compact the sample of fibers inserted inside it and a retracted, position outside of the hollow cylinder 602.

The supply conduit 604 and one of the two first pistons communicate with a same open end of the hollow cylinder 602 by means of a fitting 607 fixed to the frame 601.

Figure 11:
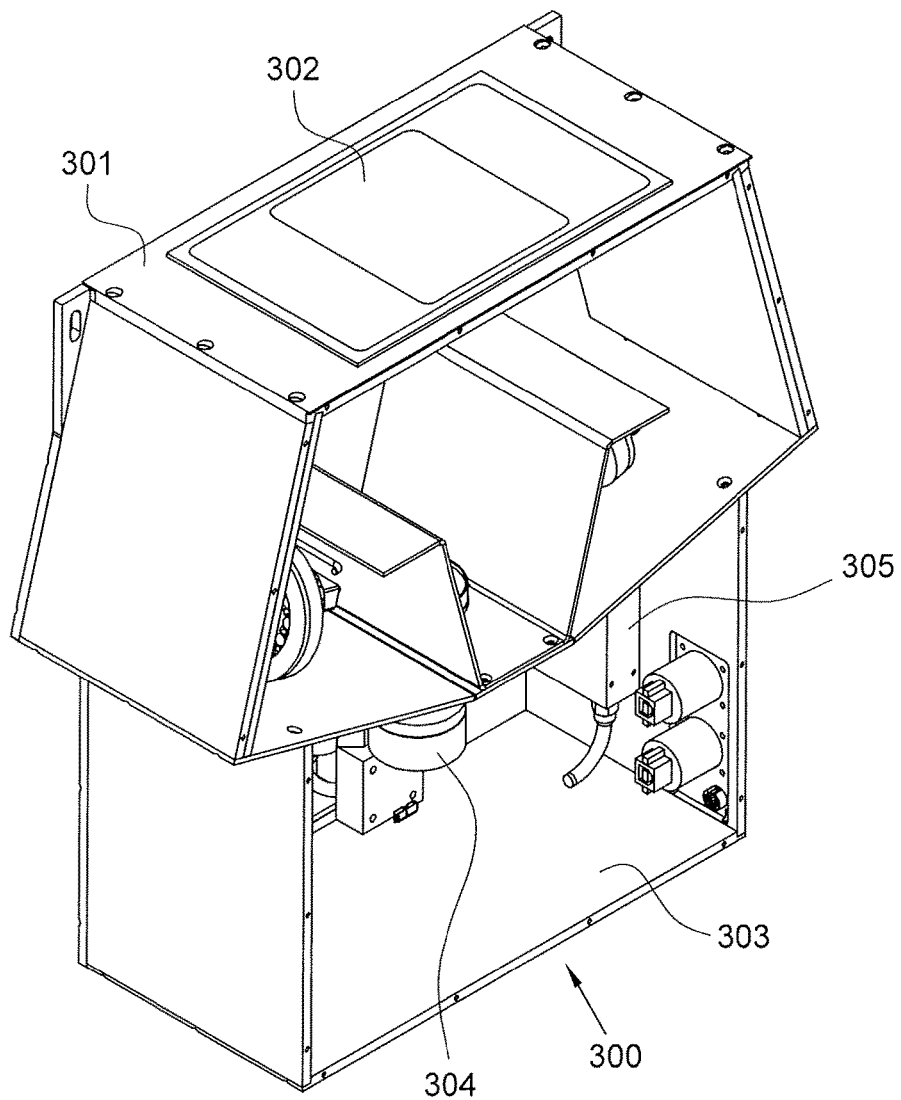
FIG. 11 is an axonometric view of a detail of the apparatus of FIGS. 1 and 2 consisting of a measuring device for measuring the color and for detecting impurities of the textile fibers.
Figure 12C:
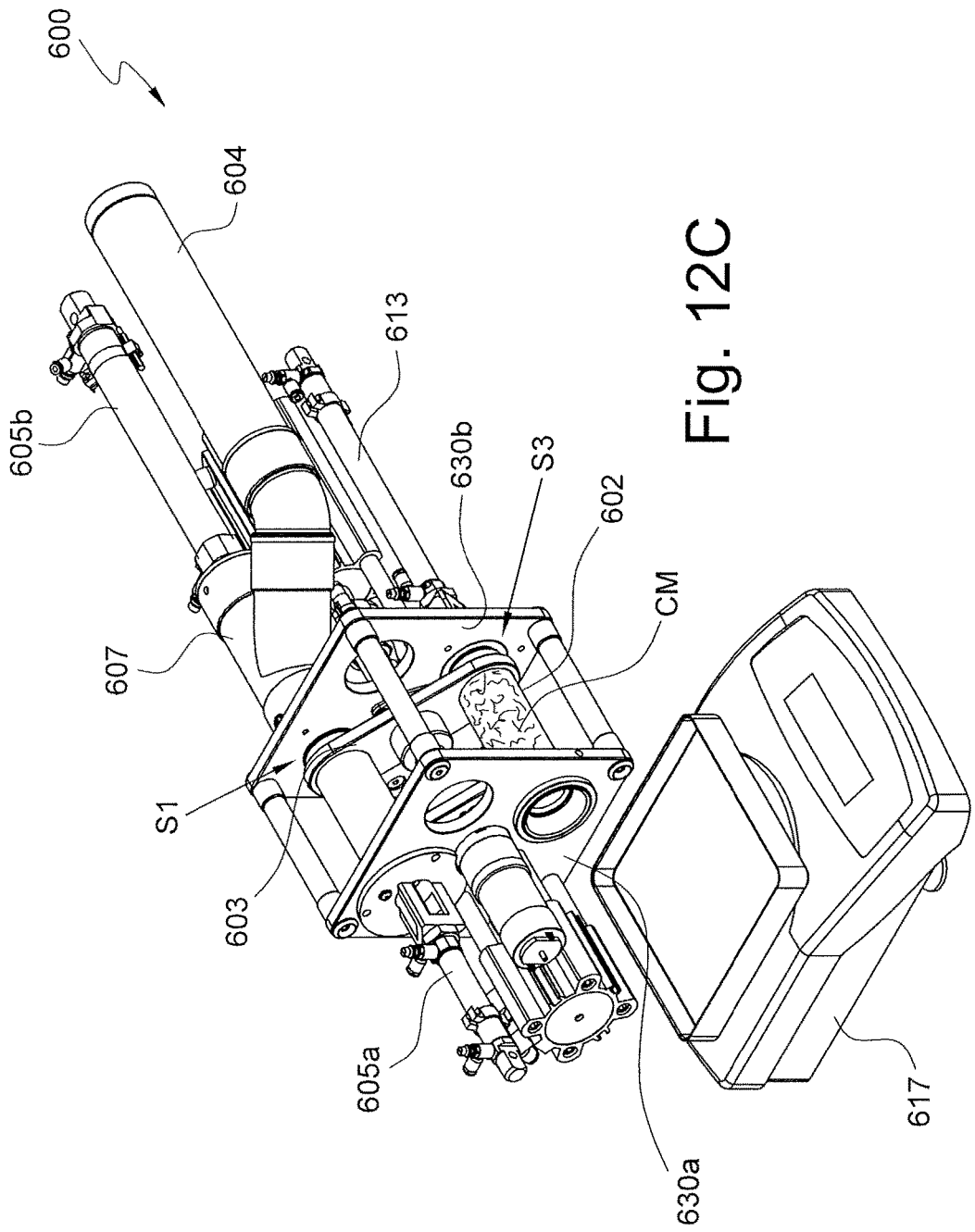
Figure 13:
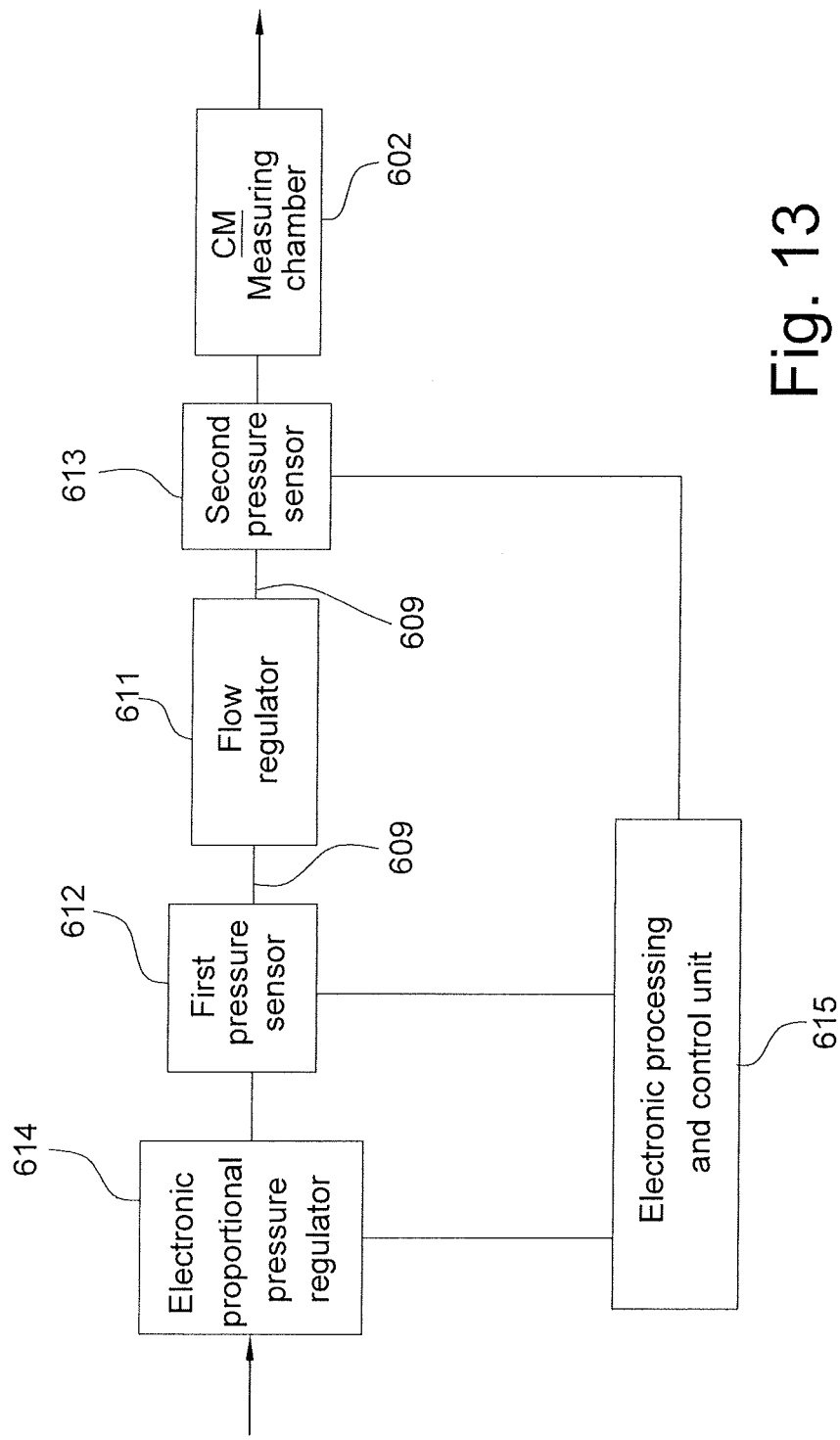
FIG. 13 is a diagram of the control system of the measuring device for measuring the fineness and maturity of cotton fibers.

The measuring station S2 comprises a pair of second pistons aligned with and opposite each other and able to be inserted into the apposite ends of the hollow cylinder 602 to respectively form a first base and a second base. These second pistons and, consequently, the first base and the second base formed by them, are of the air permeable type; for example, they can be of the type perforated with calibrated holes. The second pistons are actuated by a respective second linear actuator 608A and 608B between at least one position extended into the hollow cylinder 602 and a retracted position outside the hollow cylinder 602. A supply conduit 603 (only schematized in FIG. 11) feeds an air flow entering the hollow cylinder 602 by means of the second piston that defines the first base. The air flow fed to enter the hollow cylinder 602 comes out of it through its second base that communicates with the external environment at ambient pressure.

The supply conduit 609 has an inlet end associable with an air flow source (not shown) and an outlet end associated with a mouth 610 with which the second piston that defines the first base of the hollow cylinder 602 is associated.

Along the supply conduit 609 a flow regulator 611 is arranged, interposed between the inlet end and the outlet end of the supply conduit 609 itself. The flow regulator 611 for example consists of a throttle valve of the known type.

Along the supply conduit 609 two pressure sensors are also arranged: a first pressure sensor 612 for detecting the air pressure, which is arranged upstream of the flow regulator 611, and a second pressure sensor 613 for detecting the air pressure, which is arranged downstream of the flow regulator 611 and upstream of the first base of the measuring chamber CM.

Advantageously, moreover, an electronic proportional pressure regulator 614 is arranged along the supply conduit 609 upstream of the first pressure sensor 612 for regulating the air pressure in the supply conduit 603.

The first pressure sensor 612, the second pressure sensor 613 and the electronic proportional pressure regulator 614 are connected to an electronic processing and control unit 615 that is programmed to control the electronic proportional pressure regulator 614 as a function of the detections of the first pressure sensor 612 and of the second pressure sensor 613 or of the second pressure sensor 613 alternatively and respectively to keep the difference between the air pressure upstream and downstream of the flow regulator 611 or the air pressure entering the measuring chamber CM substantially constant and equal to a predeterminable value. It is thus possible to operate under substantially constant flow or pressure conditions at the ends the measuring chamber CM as required by standards ASTM D1448-11 for carrying out measurements of fineness and maturity, from which the Micronaire index is then obtained.

In other words, the electronic proportional pressure regulator 614 is selectively and alternatively controlled by the unit 615 to keep the pressure difference upstream and downstream of the flow regulator 611 substantially constant and equal to a predetermined value, so as to operate with a substantially constant flow.

Otherwise, the electronic proportional pressure regulator 614 is selectively and alternatively controlled by the unit 615 to keep the pressure at the ends the measuring chamber CM and, therefore, the pressure entering it substantially constant and equal to a predetermined value.

It is thus possible to operate under actual conditions of constant air flaw or of constant pressure at the ends the measuring chamber CM and equal to a predetermined value.

In fact, it is specified that at the measuring station S2, the second base of the hollow cylinder 602 communicates with the external environment, so that the detections of the second pressure sensor 613 are relative to atmospheric pressure and provide a measurement of the pressure at the ends the measuring chamber CM.

The extraction station S3 comprises a third piston insertable into one of the two opposite ends of the hollow cylinder 602. The third piston is actuated by a respective third linear actuator 616 that is movable between a retracted position outside of the hollow cylinder 602 and a position extended into the hollow cylinder 602 in order to push the fibers therein contained out of the opposite open end thereof. This makes the extraction of the fibers from the measuring chamber CM particularly simple.

The fibers expelled from the hollow cylinder 602 fall onto a scale 617 that detects the weight thereof.

The operation of the measuring device 600 can be immediately understood by the person skilled in the art from the above description and from the attached figures.

In brief, the carousel 603 carries the hollow cylinder 602 at the insertion station S1 where it is filled with a known quantity of fibers, which are compacted by means of the first pistons.

The carousel 603 carries the hollow cylinder 602 thus filled at the measuring station S2 at which the measurements of the pressure drop at the ends of the measuring chamber CM crossed by an air flow are carried out according to known protocols. These measurements, which can be repeated on the same sample under different compacting conditions, can be carried out under conditions of substantially constant flow or of substantially constant pressure.

The carousel 603 then carries the hollow cylinder 602 at the extraction station S3 at which the sample is pushed out of the hollow cylinder 602 by means of the pushing action, exerted on it by the third piston. The sample falls onto the plate of the scale 617 and is weighed.

The measurements carried out are then processed with known algorithms for determining fineness, maturity and Micronaire index.

The device for measuring stickiness, imperfections and impurities of textile fibers, in particular, cotton fibers, thus conceived can undergo numerous modifications and variants, all of which are covered by the invention; moreover, all of the details can be replaced by technically equivalent elements. In practice, the materials used, as well as the sizes, can be whatever according to the technical needs.

The invention claimed is:

1. A measuring device for measuring stickiness, imperfections and impurities in textile fibers, said device comprising a housing inside which the following are placed:
   a pair of rollers arranged side by side to one another and rotating in opposite senses and between which a web of cotton fibers is made to pass,
   heating means for heating said rollers,
   detection means for detecting the sticky fractions of said web that adhere to said rollers after the passage of said web,
   removal means for removing from said rollers said sticky fractions adhering thereto,
   a processing and control unit,
   temperature sensor means associated with said rollers,
   wherein the operation of said heating means is controlled by the processing and control unit as a function of the temperature of said rollers as detected by the temperature sensor means so as to keep the temperature of an outer side surface of said rollers close to a preset value during a stickiness measurement operation,
   wherein said heating means comprise for each roller of said pair of rollers: at least one contact body that is guided in a movable manner towards and away from said roller in order to exert a friction action on it, and actuator means for actuating the movement of said contact body towards and away from said roller,
   wherein the removal means includes a respective contact body of the at least one contact body, for each roller of the pair of rollers,
   wherein said processing and control unit is adapted to control said actuator means as a function of the signals emitted by said temperature sensor means in order to vary the position of said at least one contact body with respect to the corresponding said roller.

2. The measuring device according to claim 1, further comprising position sensor means for detecting the position of said actuator means, wherein said processing and control unit is adapted to control said actuator means as a function of the signals emitted by said temperature sensor means and by said position sensor means.

3. The measuring device according to claim 1, wherein said at least one contact body comprises a brush roller that is rotatably supported by a support bracket that has a first portion coupled to said housing in a rotatable manner about an axis parallel to a rotational axis of said brush roller and a second portion that is articulated to said actuator means.

4. The measuring device according to claim 3, wherein said brush roller is driven in rotation by a brush roller motor means that are controlled and operated by said processing and control unit.

5. The measuring device according to claim 1, wherein at least one of said rollers is supported in a movable manner towards and away from the other one along a direction orthogonal to a longitudinal axes thereof and is coupled to means for actuating such movement, and wherein the measuring device includes pressure sensors configured to detect, directly or indirectly, the contact pressure between said two rollers, wherein said electronic processing and control unit is configured to control said means for actuating the mutual movement of said two rollers as a function of the signals detected by said pressure sensors so as to keep the contact pressure between said two rollers substantially constant and close to a preset value.

6. The measuring device according to claim 1, further comprising card means for preparing said web of textile fibers and that are arranged upstream, with respect to the feed sense of said web, of said pair of rollers, acquisition means for acquiring images of said web that are interposed between said card means and said pair of rollers, means for processing the images acquired by said acquisition means that are connected to said processing and control unit and that are programmed to detect and characterize at least one of imperfections and impurities of said web, and dragging means for dragging said web along the path defined by said card means, said acquisition means and said pair of rollers.

7. A modular apparatus for measuring a plurality of characteristics of textile fibers, said apparatus comprising:
- a plurality of modules each comprising at least one measuring device for measuring at least one characteristic of said textile fibers; and
- a central processing and control unit for controlling said modules,
- wherein one of said modules comprises a measuring device according to claim 1, and
- wherein the processing and control unit is connected to the central processing and control unit.

8. The measuring device according to claim 1, wherein the textile fibers are cotton fibers.

9. The measuring device according to claim 1, wherein the preset value is 38° C. to 40° C.

* * * * *